United States Patent
Maruo et al.

(10) Patent No.: US 7,727,367 B2
(45) Date of Patent: Jun. 1, 2010

(54) BIOSENSOR AND METHOD FOR MANUFACTURING SAME

(75) Inventors: Masaharu Maruo, Moriyama (JP);
Tetsuji Deguchi, Moriyama (JP)

(73) Assignee: Gunze Limited, Kyoto (JP)

(*) Notice: Subject to any disclaimer, the term of this patent is extended or adjusted under 35 U.S.C. 154(b) by 1170 days.

(21) Appl. No.: 10/524,380

(22) PCT Filed: Aug. 8, 2003

(86) PCT No.: PCT/JP03/10117
§ 371 (c)(1),
(2), (4) Date: Feb. 11, 2005

(87) PCT Pub. No.: WO2004/017057
PCT Pub. Date: Feb. 26, 2004

(65) Prior Publication Data
US 2005/0265897 A1 Dec. 1, 2005

(30) Foreign Application Priority Data
Aug. 13, 2002 (JP) .................. 2002-235697
Jan. 9, 2003 (JP) .................. 2003-003549

(51) Int. Cl.
*G01N 27/327* (2006.01)
(52) U.S. Cl. .............. 204/403.02; 204/403.04
(58) Field of Classification Search ..................
204/403.01–403.15; 205/777.5, 778, 792
See application file for complete search history.

(56) References Cited

U.S. PATENT DOCUMENTS 6,299,757 B1 * 10/2001 Feldman et al. ........... 205/775
6,447,657 B1 * 9/2002 Bhullar et al. ........... 204/403.01

FOREIGN PATENT DOCUMENTS

| EP | 0 884 392 A1 | 12/1998 |
| JP | 03-202764 | 9/1991 |
| JP | 05-505459 | 8/1993 |
| JP | 2001-511881 | 8/2001 |
| JP | 2001-281202 | 10/2001 |

(Continued)

OTHER PUBLICATIONS

Definition of "corner" downloaded from www.merriam-webster.com on Apr. 23, 2009.*

*Primary Examiner*—Alex Noguerola
(74) *Attorney, Agent, or Firm*—Knobbe Martens Olson & Bear LLP

(57) ABSTRACT

The present invention provides a biosensor that can be used for easy and quick quantitative analysis of a specific component in a sample with high precision and a method for manufacturing such a biosensor. The present invention also provides a biosensor that can be used for a highly precise quantitative analysis after an extended period of storage, specifically, a biosensor with excellent storage stability, and a method for manufacturing such a biosensor. The present invention relates to a biosensor comprising an electrically insulating substrate (1); an electrode (2) having a working electrode (21) and a counter electrode (22) formed on the substrate; and a reaction part (4) that is adhered to one end of the electrode (2); the reaction part (4) being mainly composed of a hydrophilic polymer comprising an oxidoreductase, an electron acceptor, fine crystalline cellulose powder, and hydrophilic and hydrophobic segments.

5 Claims, 10 Drawing Sheets

FOREIGN PATENT DOCUMENTS

| | | |
|---|---|---|
| JP | 2001-518620 | 10/2001 |
| JP | 2001-311712 | 11/2001 |
| JP | 2001-356108 | 12/2001 |
| WO | WO 91/09139 A1 * | 6/1991 |
| WO | WO 97/02487 A1 * | 1/1997 |
| WO | WO 99/17155 A1 * | 4/1999 |
| WO | WO 01/36955 A1 | 5/2001 |

* cited by examiner

Fig. 5  Comparison of Faraday current

Fig. 6 Comparison of sensor output

BIOSENSOR AND METHOD FOR MANUFACTURING SAME

This application is the U.S. National Phase under 35 U.S.C. §371 of International Application PCT/JP2003/010117, filed Aug. 8, 2003, which claims priority to Japanese Patent Application No. 2002-235697, filed Aug. 13, 2002, and No. 2003-3549, filed Jan. 9, 2003. The International Application was not published under PCT Article 21(2) in English.

TECHNICAL FIELD

The present invention relates to a biosensor with which a high-precision quantitative analysis of a specific component in a sample can be easily and quickly conducted, and a method for manufacturing the same.

BACKGROUND ART

A biosensor is used as a tool for readily determining the quantity of a specific component in a sample solution without diluting and/or stirring the sample solution. Many techniques for overcoming problems of heretofore-used biosensors have been reported.

For example, Japanese Unexamined Patent Publication No. 1991-202764 discloses a method for improving measurement accuracy by adding a hydrophilic polymer to a reaction layer. However, potassium ferricyanides are deposited in the glucose sensor disclosed in Japanese Unexamined Patent Publication No. 1991-202764, the shapes of the obtained reaction parts are not uniform, and therefore the measurement accuracy thereof is insufficient.

There is a technique wherein fine crystalline cellulose is made to coexist in a system having an enzyme and an electronic mediator as a reaction layer (Japanese Unexamined Patent Publication No. 2001-311712). The enzyme sensor disclosed in Japanese Unexamined Patent Publication No. 2001-311712 enhances the uniformity of the thickness of the reaction layer, the precision of the sensor chip, and the performance stability of the chip. However, the fine crystalline cellulose has low solubility in the sample, and therefore it takes time for the fine crystalline cellulose to be satisfactorily dissolved in or mixed with the sample. The measurement thus takes too long. It is presumed that one of the reasons for this problem is that large crystals of potassium hexacyanoferrate (III) grow and the surface area of the reaction layer which can contact the sample become small, and this makes the dispersion and dissolution of the fine crystalline cellulose difficult.

Japanese Unexamined Patent Publication No. 2001-281202 discloses a method wherein a reaction layer is formed by a sublimation method. However, this method requires decompression in the biosensor manufacturing process. This increases costs of facilities, etc., and therefore this method is not suitable for manufacturing a biosensor at low cost. Furthermore, this makes the manufacturing operation complicated, resulting in low productivity.

DISCLOSURE OF THE INVENTION

An object of the present invention is to provide a biosensor with which a high-precision quantitative analysis of a specific component in a sample solution can be easily and quickly conducted and a method for manufacturing such a biosensor. Another object of the present invention is to provide a biosensor that can be used for a highly precise quantitative analysis after extended storage, specifically, a biosensor with excellent storage stability, and a method for manufacturing such a biosensor. Still another object of the present invention is to provide a biosensor with a simple structure that can smoothly introduce a liquid sample without leaving bubbles in the holding space of the liquid sample and without providing an outlet for discharging gas in the holding space.

The present inventors conducted intensive research to achieve the above objects, and found that, by employing a deposition method applying a pigment production technique, and producing fine particles of the crystalline compound used in the reaction part of the biosensor, it is possible to increase the dispersion/dissolution ability of the sensor chip reaction part in the sample and shorten the reaction time. The present invention is accomplished by further applying these findings.

The present invention provides a biosensor (hereunder sometimes referred to as "a biosensor of the first invention") and a method for manufacturing such a biosensor as described below.

Item 1. A method for manufacturing a biosensor provided with an electrically insulating substrate (1); an electrode (2) having a working electrode (21) and a counter electrode (22) formed on the substrate; and a reaction part (4) that is adhered to one end of the electrode (2), the reaction part comprising an oxidoreductase, an electron acceptor, and fine crystalline cellulose powder;

the method comprising the following sequential steps of (A1) to (C1):

(A1) a step of forming the electrode (2) by disposing a working electrode (1) and a counter electrode (2) on the electrically insulating substrate (1) in parallel and in close proximity;

(B1) a step of preparing an application liquid for forming reaction part, by preparing a mixed solution A comprising a good solvent and three components consisting of an oxidoreductase, an electron acceptor, and fine crystalline cellulose, and then adding the mixed solution A dropwise to a poor solvent, while stirring, to produce dispersion B; and (C1) a step of forming the reaction part (4) by applying the application liquid for forming reaction part prepared in the step (B1) to one end of the electrode (2) on the electrically insulating substrate (1) obtained in the step (A1) and drying it.

Item 2. A manufacturing method according to Item 1, wherein the electrode is formed of at least one member selected from the group consisting of platinum, gold, palladium, and indium-tin oxides.

Item 3. A biosensor obtainable by a manufacturing method of Item 1 or 2.

Item 4. A method for measuring the glucose component, alcohol component, lactic acid component or uric acid component in a sample solution using the biosensor of Item 3.

The present inventors also found that a biosensor having excellent storage stability can be obtained by making a specific hydrophilic polymer component coexist in the reaction part of the above-described biosensor, and accomplished the present invention by further applying these findings.

In other words, the present invention provides a biosensor (hereunder sometimes referred to as "a biosensor of the second invention") and a method for manufacturing such a biosensor as described below.

Item 5. A biosensor comprising an electrically insulating substrate (1); an electrode (2) having a working electrode (21) and a counter electrode (22) formed on the substrate; and a reaction part (4) that is adhered to one end of the electrode (2); the reaction part (4) being mainly composed of an oxidoreductase, an electron acceptor, fine crystalline cellulose powder, and a hydrophilic polymer containing hydrophilic and hydrophobic segments.

Item 6. A biosensor according to Item 5, wherein the hydrophilic polymer is composed of a straight-chain oxyalkylene segment(s) and an alkyl group-branched oxyalkylene segment(s).

Item 7. A biosensor according to Item 6, wherein the average molecular weight of the alkyl group-branched oxyalkylene segment in the hydrophilic polymer is 1500 to 4000, and the content of the straight-chain oxyalkylene segment(s) among all polymer molecules is 30 to 80 wt %.

Item 8. A biosensor according to any one of Items 5 to 7, wherein the reaction part (4) is formed by coating a dispersion comprising an oxidoreductase, an electron acceptor, fine crystalline cellulose, and a hydrophilic polymer composed of hydrophilic and hydrophobic segments.

Item 9. A method for manufacturing a biosensor according to Item 8, which comprises the following sequential steps of (A2) to (C2);
- (A2) a step of forming an electrode (2) by disposing a working electrode (21) and a counter electrode (22) in parallel and in close proximity on an electrically insulating substrate (1);
- (B2) a step of preparing an application liquid for forming reaction part by preparing a mixed solution Ma comprising a good solvent and three components consisting of an oxidoreductase, an electron acceptor, and fine crystalline cellulose, then adding the mixed solution Ma dropwise to a polymer solution Pa containing the hydrophilic polymer dissolved in a solvent that has poor solubility with the three components but good solubility with the hydrophilic polymer, while stirring, to prepare a dispersion; and
- (C2) a step of forming the reaction part (4) by applying the application liquid for forming reaction part prepared in the step (B2) to one end of the electrode (2) on the electrically insulating substrate (1) obtained in the step (A2) and drying it.

Furthermore, the present inventors found that, in a biosensor wherein an electrically insulating substrate and a cover sheet are disposed in the tip portion in such a manner that they face each other with a space in between and a spacer sheet somewhere therebetween, by providing a projection at one side of the spacer sheet end in the holding space of the liquid sample, with the projection extending toward the end of the sensor chip, it is possible to introduce the liquid sample into the holding space without leaving bubbles. The inventors accomplished the present invention by further applying this finding.

The present invention provides a biosensor (hereunder sometimes referred to as "a biosensor of the third invention") and a method for manufacturing the same as explained below.

Item 10. A biosensor comprising:
  in its tip portion, an electrically insulating substrate (1) and a cover sheet (6) facing each other with a space in between and a spacer sheet (5) somewhere therebetween; and a reaction part (4) having an oxidoreductase in a holding space (S) formed by the substrate, the cover sheet and the spacer sheet end;

the liquid sample being delivered from the tip of the sensor into the holding space by capillary action, and an electrochemical change caused by an enzyme reaction between the liquid sample and the reaction part (4) being detected using an electrode (2) having a working electrode (21) and a counter electrode (22); and the biosensor being provided with a projection (51) at one side of the spacer sheet end in the holding space (S) with the projection extending toward the end of the biosensor.

Item 11. A biosensor according to Item 10, wherein an inside corner part (52) is formed on the spacer sheet end.

The present invention is explained in detail under the three headings of "biosensor of the first invention, "biosensor of the second invention" and "biosensor of the third invention".

I. Biosensor of the First Invention

Biosensor of the First Invention

A biosensor of the first invention is explained in detail with reference to FIG. 1, which illustrates one embodiment of the first invention. The present invention provides a method for manufacturing a biosensor comprising an electrically insulating substrate (1), an electrode (2) having a working electrode (21) and a counter electrode (22) provided on the substrate, and a reaction part (4) that is adhered to one end of the electrode, the reaction part comprising an oxidoreductase, an electron acceptor, and fine crystalline cellulose powder. The biosensor of the present invention uses a deposition method that includes application of a pigment production technique during the process of forming the reaction part. This makes it possible to form a reaction part of uniform fine crystals, thus obtaining high dispersibility and solubility of reaction part in the sample solution.

The electrode (2) of a signal-converting unit that composes the hardware part of the biosensor of the first invention is first explained.

The electrode (2) is composed of a working electrode (21) (also referred to as a measuring electrode) and a counter electrode (22) (with a reference electrode provided if necessary) forming a pair, in parallel and in close proximity, and is disposed on an electrically insulating substrate (1). Examples of the substrate are polyethylene terephthalate (PET), polyethylene naphthalate, biodegradable polyesters composed of an aliphatic unit, an aromatic unit, and like polyester-based resin films; polyamide-imide film, polyimide and like plastic films having excellent heat resistance, chemical resistance, strength, etc.; and ceramic and like inorganic substrates. The thickness is in the range of about 50 to 200 μm.

Usually a plastic film is used for the substrate; however, because of its production ease, heat resistance, chemical resistance, strength and like desirable properties, a two-layered substrate obtained by laminating a polyester-based resin film and a polyimide film may be used.

When a polyester-based resin film is used, from the viewpoint of transparency, etc., it is preferable that the substrate be made white by kneading titanium oxide and the like therein.

The working electrode (21) and the counter electrode (22) are formed of platinum, gold, palladium, indium-tin oxide and like good electrical conductors on the substrate (1) (directly or indirectly). As a production method, hot stamping may be employed; however, vacuum deposition or sputtering is more preferable since it allows a fine electrode pattern to be formed quickly with high precision. When sputtering is employed, the electrodes can be formed in a single step by masking the area outside of which both electrodes will be formed.

It is also possible to obtain the electrodes by covering the entire surface of the substrate with a thin film formed from a good electrical conductor(s) and patterning it into the shape of the electrodes by photoetching.

The thickness of the electrode varies depending on the specific resistance of the good electrical conductor; however, it should not be thicker than necessary. Usually, a thickness of about 30 to 150 nm is enough.

The electrode is basically stripe-shaped with the working electrode (21) and the counter electrode (22) being disposed on the substrate in parallel and in close proximity. Usually, the shape of the end of the electrode on which the reaction part (4) is disposed is a simple strip; however, it is also possible to provide, for example, a curvature thereto to increase the contact area with the reaction part.

Note that the other end of the electrode serves as a terminal connected to an electrical potential scanner that is stored in a measuring device, and usually it may be detachable to the measuring device.

The reaction part (4) provided on one end of the electrode (2) is formed by applying a mixed solution comprising three components described later in a reaction part cell (31) disposed in a mask sheet (3). The reaction part (4) is formed in the reaction part cell (31) so as to cover both the working electrode (21) and the counter electrode (22), so that the mixed solution of the three components will not leak to other parts.

FIG. 1 schematically illustrates the structure of a signal-converting unit. In FIG. 1, the signal-converting unit comprises a strip-shaped working electrode (21) and counter electrode (22) arranged on an electrically insulating substrate (1) in parallel and in close proximity. A mask sheet (3), an electrically insulating spacer sheet (5), and a cover sheet (6) are laminated on the electrodes sequentially. A reaction part cell (31) is formed in the mask sheet (3), and a reaction part (4) composed of three components described later is formed therein. The spacer sheet (5) has a projection (51) formed on one side of the sensor end (curved), and has an inside corner part (52) provided on the basal portion of the projection. The spacer sheet (5) is covered with an electrically insulating cover sheet (6). A sample suction port (15) connecting to the reaction part (4) is formed.

The suction amount and ease of suction of the sample depend on the shape, cross section area, and the like of the sample suction port. The volume of the reaction part (4) depends on the thickness of the mask sheet (3) and the area of the reaction part cell (31). Suitable conditions can be selected by varying the thickness of the mask sheet (3) and the area of the reaction part cell (31).

The reaction part (4) is explained below.

The reaction part (4) is a film (or layer) that mainly comprises three components, i.e., an oxidoreductase, an electron acceptor, and fine crystalline cellulose.

Each component is described below.

The oxidoreductase is a primary component that contacts the liquid sample and detects a specific component in the liquid sample by selectively reacting with it due to oxidation-reduction. Therefore, the oxidoreductase is an essential component. Examples of the components that selectively react with an enzyme due to oxidation-reduction are a glucose component, an alcohol component, a lactic acid component, and a uric acid component. All of these components do not react with one specific enzyme but the enzyme that selectively reacts with each component is used.

For example, glucose selectively reacts with glucoseoxidase, and the reaction is actually conducted under the presence of water and oxygen to generate gluconic acid and hydrogen peroxide. When the alcohol component is measured, alcoholoxidase or alcoholdehydrogenase is used. When the lactic acid component is measured, lactic acid oxidase or lactic acid dehydrogenase is used. When the uric acid component is measured, uricase is used.

However, the use of only the above-mentioned enzymes usually results in a slow detection response and low measurement precision, and therefore, an electron acceptor (sometimes referred to as an electronic mediator) is usually included to compensate for the drawbacks of the enzymes. Typical example of a biosensor having an electron acceptor included therein is a glucose sensor, which is used, for example, for measuring the blood-sugar level of a blood sample.

The electron acceptor is usually an organic or inorganic fine powder compound that accelerates the oxidation-reduction reaction of the enzyme. Specifically, alkali metal ferricyanides (potassium metal salt is particularly preferable), ferrocene or its alkyl substituted product, p-benzoquinone, methylene blue, 4-potassium □-naphthoquinone sulfonate, phenazine methosulfate, 2,6-dichlorophenol indophenol, etc., are used. Alkali metal ferricyanides and ferrocene-based compounds are especially effective. This is because they function stably as an electron transfer medium and dissolve easily with water-based solvents such as water, alcohols or a mixture thereof.

Note that the size of the electron acceptor powder particles is about 5 to 100 μm.

It is also possible to obtain a practically usable sensor by using a reaction part that comprises only the above-described two components. However, a biosensor obtained by applying an aqueous solution composed of these two components to the electrode tends to exhibit variations in measurement precision depending on the conditions used. In other words, it is difficult to obtain a biosensor that exhibits constant performance. The reason for this is unknown; however, it is assumed that a crystal structure deposited after the application of the solution is one of the reasons.

The fine crystalline cellulose as the third component is added so as to reduce the variation in the measurement precision. There are several factors that contribute to reducing this variation. Examples of such factors are as follows:

The electrochemical reaction between the electrode and the electron acceptor is reduced due to the reduced chance of the electron acceptor directly contacting the electrode; enzyme particles and electron acceptor particles are dispersed finely and uniformly; when blood is used as a sample, even if a small number of blood corpuscles are included in the blood plasma, the cellulose can absorb the corpuscles; dispersion of the two components outside of the system is reduced due to the cellulose network, etc. It is presumed that these factors synergetically interact each other and, as a result, variations in the measurement precision are reduced.

The fine crystalline cellulose is in the form of fine particles obtained by extracting crystallite from plant fiber, and usually the particle diameter is about 10 μm or less and the length is 300 μm or less. The thus obtained fine crystalline cellulose is a primary component; however, amorphous cellulose fine powder obtained at the same time may be mixed thereinto.

Method for Manufacturing the Biosensor of the First Invention

The method for manufacturing the biosensor of the first invention comprises the following sequential steps of (A1) to (C1) as described below:

(A1) a step of forming the electrode (2) by disposing a working electrode (21) and a counter electrode (22) in parallel and in close proximity on the electrically insulating substrate (1);

(B1) a step of preparing an application liquid for forming reaction part, by preparing a mixed solution A comprising a good solvent and three components consisting of an oxidoreductase, an electron acceptor, and fine crystalline cellulose, and then adding the mixed solution A to a poor solvent, while stirring, to produce dispersion B; and (C1) a step of forming the reaction part (4) by applying the application liquid for forming reaction part that is prepared in the step (B1) to one end of the electrode (2) of the electrically insulating substrate (1) obtained in the step (A1) and drying it.

One of the main features of the above-described method is the employment of a deposition method that includes the application of a pigment production technique in the step (B1) of preparing the composition of the reaction part (4). Therefore, a reaction part with uniform fine crystals is formed and this makes it possible to increase the dispersion/dissolution ability of the sensor chip reaction part in the sample.

First, the step (A1) of forming the electrode (2) is explained below. A working electrode (21) and a counter electrode (22) are provided in parallel and in close proximity on an electrically insulating substrate (1), forming the electrode (2).

There are various methods for forming the electrode (2) on the electrically insulating substrate (1), for example, an electrode pattern can be provided on the substrate (1) by hot stamping, direct vacuum deposition, sputtering, etc.; the electrode pattern can be formed by photoetching; and an electrode tape containing an electrically conductive material can be adhered to the substrate (1).

A specific example of the method for adhering an electrode tape containing an electrically conductive material to the substrate (1) is explained below. Platinum, gold, palladium, indium-tin oxide or other electrically conductive material is deposited or sputtered onto a thin polyimide, aromatic polyimide or other plastic electrically insulating material sheet having supporting properties and excellent heat resistance, and the back surface of the electrically insulating material sheet is coated with ethylenevinyl acetate or other heat-sealable material. The thus obtained multi-layered sheet is cut into a tape form and used as an electrode tape. The thus obtained electrode tape is heat-sealed to the electrically insulating substrate (1), forming the electrode (2).

An example of the method for providing an electrode pattern by sputtering, etc., is explained below. When both electrodes have a stripe shape, a mask plate stamped with two stripe-shaped parallel holes is used as a masking material during sputtering, and this mask plate is fixed to the top surface of a polyimide film leaving no space between the mask plate and the polyimide film. Sputtering is started and platinum is injected onto the film through the stripe-shaped window, and then two continuous stripe-shaped electrodes are closely adhered onto the polyimide film. The electrode (2) is formed by laminating the polyimide film containing the electrodes formed thereon with a PET film through an adhesive.

Alternatively, the electrode (2) can be formed by directly sputtering an electrically conductive material onto the electrically insulating substrate (1)(for example, a PET film).

Next, the step (B1) of preparing the application liquid for forming reaction part is explained below.

The reaction part-forming application liquid of the present invention is composed of a reaction reagent comprising three components, i.e., an oxidoreductase, an electron acceptor, and fine crystalline cellulose powder. Because the reaction reagent comprises fine crystalline cellulose powder, an excellent film forming ability for forming the reaction part can be obtained. The components mentioned above can also be used as the three components.

Good solvents for the present invention are those in which oxidoreductases and electron acceptors are highly soluble, and aqueous good solvents such as water or water-containing solvents are preferable. Examples of water-containing solvents are mixed solutions of water and a solvent(s) compatible with water, such as methanol, ethanol, dioxane, isopropyl alcohol, etc.

Poor solvents for the reaction reagent of the present invention are those that are water soluble and that reduce the solubility of the oxidoreductase and the electron acceptor, such as alkylene glycol monoalkyl ether, alkylene glycol, propylene alcohol, butanol, etc. Among these, ethylene glycol monoethyl ether (cellosolve) is preferable.

Some portion of the reaction reagent comprising the three components may be dissolved in the dispersion B obtained in the above-described step (B1). Specifically, two components, i.e., the oxidoreductase and the electron acceptor, may be substantially dissolved therein. All that is necessary for the fine crystalline cellulose powder is that it exists as a dispersion or a suspension.

A preferable combination of a good solvent and a poor solvent is that of water and ethylene glycol monoethyl ether. The volume ratio of the good solvent to the poor solvent is usually about 1:0.5 to 10, and preferably about 1:1 to 3.

A specific example of the electrode formation step (B1) is explained below. An aqueous suspension of fine crystalline cellulose is stirred by a homogenizer, an oxidoreductase (glucose oxidase or the like) and an electron acceptor (potassium ferricyanide or the like) are added to the suspension, and the suspension is stirred, producing a mixed solution A. One embodiment is such that, for example, 0.1 to 10 g of glucose oxidase, 5 to 70 g of potassium ferricyanide, and 1 to 10 g of fine crystalline cellulose are added to 100 ml of 100% water to obtain a mixed solution A. The mixed solution A is added dropwise to a poor solvent (ethylene glycol monoethylether, etc.), while stirring, to prepare a dispersion B. The thus obtained dispersion is to be applied to the reaction part.

When the dispersion B is prepared by the above deposition method, the faster the precipitation speed is, the finer the crystals will be. From the viewpoint of ease in the drying step for the reaction part (4), it is preferable to select a good solvent and a poor solvent whose boiling points are close to each other.

Finally, the step of forming the reaction part (C1) is explained next. A film is formed by adding and applying a certain amount of the application liquid for forming reaction part to one end of the electrode (2) on the electrode formed plate obtained in the above-described (A1) and drying it.

Specifically, a mask sheet (3) is heat-sealed to an electrically insulating substrate (1) having a working electrode (21) and a counter electrode (22) in parallel and in close proximity. The mask sheet (3) is composed of a heat sealable sheet and provided with a reaction part cell (31) for controlling the electrode area in the sensor chip reaction part. In other words, the reaction part cell (31) is formed in such a manner that a window is provided on the end of the sensor through which a portion of the working electrode (21) and the counter electrode (22) can be seen.

The application liquid for forming reaction part comprising three components, which is obtained in step (B1), is applied inside the reaction part cell (31) in the mask sheet (3) disposed on the electrically insulating substrate (1). The application liquid for forming reaction part is applied so as to cover both the working electrode (21) and the counter electrode (22). The liquid is applied thereto using a pipet, nozzle, etc., then is placed in an oven or the like for a certain time, and dried to form a film. The thus formed film is adhered over both the working electrode (1) and the counter electrode (2), and functions as the reaction part (4).

The electrically insulating spacer sheet (5) and cover sheet (6) are deposited on the mask sheet (3) sequentially. The spacer sheet (5) has a projection (51) formed on one side of the sensor end (curved), and has an inside corner part (52) is provided on the basal portion of the projection. Due to the projection (51), when the sensor of the present invention contacts the sample solution, it is possible to smoothly introduce a liquid sample to the holding space by capillary action without leaving bubbles in the holding space. All that is necessary for the spacer sheet (5) is that the sheet has adhesiveness on both sides and a uniform thickness.

An electrically insulating cover sheet (6) covers the spacer sheet (5), and a sample suction port (15) communicating with the reaction part (4) is thereby formed.

The amount and ease of sample suction depend on the shape, area of cross section or the like of the sample suction port. The volume of the reaction part (4) depends on the thickness of the mask sheet (3) and the area of the reaction part cell (31). Suitable conditions can be selected by varying the thickness of the mask sheet (3) and the area of the reaction part cell (31).

It is preferable that the reaction part be formed across the working electrode (21) and the counter electrode (22); however, the working electrode (21) and the counter electrode (22) need not be formed in substantially the same shape or location.

A desired biosensor can be obtained by following the above-described steps of (A1) to (C1), and the thus obtained biosensor is then cut into biosensor chips, thus completing the process.

II. Biosensor of the Second Invention

Biosensor of the Second Invention

A biosensor of the second invention is explained in detail with reference to FIGS. 7 to 9, which illustrate one embodiment of the second invention. A biosensor of the second invention comprises an electrically insulating substrate (1); an electrode having a working electrode (21) and a counter electrode (22) formed on the substrate; and a reaction part (4) that is adhered to one end of the electrode; the reaction part (4) being mainly composed of an oxidoreductase, an electron acceptor, fine crystalline cellulose powder, and a hydrophilic polymer comprising hydrophilic and hydrophobic segments.

The electrode (2) of a signal-converting unit that composes the hardware part of the biosensor of the second invention is the same as the "electrode (2)" described in the item "I. Biosensor of the first invention".

The reaction part (4) is explained below.

As described above, the reaction part (4) is a film (or layer) mainly comprises four components, i.e., an oxidoreductase, an electron acceptor, fine crystalline cellulose, and a hydrophilic polymer composed of hydrophilic and hydrophobic segments.

Three of the components that compose the reaction part (4), i.e., an oxidoreductase, an electron acceptor, and fine crystalline cellulose, are the same as those described in "reaction part (4)" in the item "I. Biosensor of the first invention".

The biosensor of the first invention employs a reaction part comprising these three components, and this greatly reduces measurement variations and makes it possible to measure a specific component in a sample with high precision. However, in the process of conducting several preparatory checks before using such a biosensor, it became clear that the biosensor can be further improved in the following points.

Measurement with high precision is possible when the biosensor of the first invention is used immediately after production; however, if it is used after extended storage, the measurement value tends to lower. This makes accurate measurement difficult. In other words, because the reactivity of the reaction part deteriorates with the lapse of time, there was room for improving the storage stability over extended time periods. It was also necessary to further reduce the difference between the components amount (absolute value) in the sample and the measured value and to further improve the measurement precision.

The inventors found that unsolved drawbacks of the biosensor of the first invention are overcome by adding, as the fourth component, the above-mentioned "hydrophilic polymer composed of hydrophilic and hydrophobic segments" to the reaction part of the biosensor of the first invention. The hydrophilic polymer achieves great effects only when it is used in combination with the three components, and, if one of the three components, for example, fine crystalline cellulose, is missing or replaced with another component, the objects of the present invention cannot be achieved.

The reason why adding the polymer to the three components produces such effects is unclear; however, presumably, the following working effects are attributable thereto.

By using the four components, a reaction part (4) with finer and more uniform particles is formed compared to the case where only the three components are used. Furthermore, it is possible to obtain a reaction part (4) wherein the polymer closely links the three components mutually. This reduces changes in the internal conditions of the reaction part, and makes it less influenced by external conditions (particularly dryness), thus allowing the biosensor of the present invention to achieve high stability over time. Furthermore, because the particles in the reaction part (4) are fine and the components are closely linked mutually, the reaction with a tested component progresses promptly and quantitatively, achieving measurement with high precision.

The biosensor of the second invention basically has the same structure as that of the biosensor of the first invention except that the reaction part (4) comprises the above-described four components.

The hydrophilic polymers are as follows. First, the word "hydrophilic" means the property of swelling by being dissolved or hydrated in water or water soluble aliphatic alcohols having a hydroxyl group and/or a mixture thereof.

Specific examples are alkali metal salts of polyacrylic acids, alkanol amine salts of polyacrylic acids, polyoxyalkylenes, etc. Among these, polyoxyalkylenes are preferable. Examples of polyoxyalkylenes are polyoxyethylenealkyl (hydrophilic) ether having a higher aliphatic group (hydrophobic) at one of the terminals; higher fatty acid esters (hydrophobic) of polyethylene glycol (hydrophilic); polymers of a straight-chain oxyalkylene segment (hydrophilic) and an alkyl group-branched oxyalkylene segment (hydrophobic); etc. Among these, a hydrophilic polymer of the straight-chain oxyalkylene segment and the alkyl group-branched oxyalkylene segment (hereunder referred to as "polymer A") is the most preferable.

By using the hydrophilic polymer, the above-mentioned working effects achieved by the presence of hydrophilic polymer (i.e., high stability over time, high measurement precision, etc.) can be further enhanced. Furthermore, when the polymer clearly has both hydrophilic and hydrophobic properties, it is possible to effectively conduct, particularly, the step (B2) of preparing the application liquid for forming reaction part in the biosensor production process described in Item 9, which enhances the working effects of the invention. Further, the use of the hydrophilic polymer improves the affinity between the electrode substrate and the application liquid for forming reaction part, therefore coating of the liquid becomes easy and the adhesiveness of each sheet is increased.

If a hydrophilic polymer having only hydrophilic segment(s) or only hydrophobic segment(s) is used, it is difficult to obtain effects such as high storage stability over a long time.

In the polymer A, the bond between the straight-chain oxyalkylene segment expressing hydrophilicity and the alkyl group-branched oxyalkylene segment expressing hydrophobicity may be, for example, a random bond or a mutual and regular bond (block structure). Among these, the block structure is preferable. This is because, in the block structure, the molecular weight in each unit can be easily controlled, and therefore the extent of the hydrophilicity and hydrophobicity can be clearly and easily changed.

The balance between the two properties in the polymer A can also be controlled by the molecular weight and content of each fragment. In the present invention, the molecular weight and content defined in Item 7 are preferable. The amount of the alkyl group-branched oxyalkylene segment in the hydrophilic polymer is expressed as an average molecular weight and the straight-chain oxyalkylene segment therein is expressed as wt %. Specifically, the former is preferably 1500 to 4000 and more preferably 2000 to 3000, and the latter is preferably 30 to 80 wt % and more preferably 40 to 70 wt %.

When such a hydrophilic polymer is used, a reaction part (4) without surface greasiness is formed, and therefore, even if the reaction part were to be placed in a dry condition, there is no risk that it will become too dry or adversely affect the operation of the reaction part. In other words, better storage stability can be attained.

Examples of monomer components forming the straight-chain oxyalkylene segment are ethylene oxide, 1,3-propylene oxide, 1,4-butylene oxide and like ring-opening polymerized polymer units of a straight-chain alkylene oxide. Examples of monomer components forming the alkyl group-branched oxyalkylene segment that expresses hydrophobicity are methylethylene oxide, ethylethylene oxide and like ring-opening polymerized polymer units of an alkylene oxide having a branched (side chain) alkyl group.

Basically, all that is necessary for the biosensor of the invention is that the biosensor mainly comprise the above-described four components, and in this case, it is effective that the ratio of each component be set as follows: an oxidoreductase of 0.1 to 10 wt %, and preferably 0.3 to 6 wt %; an electron acceptor of 20 to 90 wt %, and preferably 35 to 86 wt %; a fine crystalline cellulose of 1 to 30 wt %, and preferably of 3 to 20 wt %: a hydrophilic polymer of 2 to 40 wt %, and preferably of 5 to 30 wt %.

Method for Manufacturing the Biosensor of the Second Invention

The biosensor of the present invention comprises a reaction part (4) primarily containing the above-described four components, wherein the reaction part (4) and other constituent components of the biosensor synergetically interact with each other and, as a result, achieve greatly improved effects as described above (i.e., high stability over time, high measurement precision, etc.). The same level of such effects, however, is not always obtained by employing any manufacturing method. In particular, the method described in Item 9 is an example of a method for efficiently obtaining a biosensor with a level of performance higher that meets or exceeds a certain level.

Specifically, the method for manufacturing the biosensor of the second invention comprises the following sequential steps of (A2) to (C2) as described below:

(A2) a step of forming an electrode (2) by providing a working electrode (21) and a counter electrode (22) in parallel and in close proximity on an electrically insulating substrate (1);

(B2) a step of preparing an application liquid for forming reaction part, by preparing a mixed solution Ma comprising a good solvent and three components consisting of an oxidoreductase, an electron acceptor, and fine crystalline cellulose, then adding the mixed solution Ma dropwise to a polymer solution Pa containing the hydrophilic polymer dissolved in a solvent that has poor solubility with the three components but good solubility with the hydrophilic polymer, while stirring, to prepare a dispersion; and (C2) a step of forming the reaction part (4) by applying the application liquid for forming reaction part prepared in the step (B2) to one end of the electrode (2) on the electrically insulating substrate (1) obtained in the step (A2), and drying it.

The primary feature of the manufacturing method described above is, in contrast to other possible methods, that the application liquid to be coated in order to form a reaction part in Item 8 is in the form of a dispersion (or a suspension).

The electrode formation step of (A2) is a step wherein a working electrode (21) and a counter electrode (22) are formed in parallel and in close proximity on an electrically insulating substrate (1). There are various methods which can be employed for forming the electrode (2) on the electrically insulating substrate (1). Such methods include providing an electrode pattern on the substrate (1) by hot stamping, direct vacuum deposition, sputtering, etc.; forming an electrode pattern by photoetching; adhering an electrode tape containing an electrically conductive material to the substrate (1); etc.

A specific example of the method for adhering an electrode tape containing an electrically conductive material to the substrate (1) is given next. Platinum, gold, palladium, indium-tin oxide or other electrically conductive material is deposited or sputtered onto a thin polyimide, aromatic polyimide or other plastic electrically insulating material sheet having supporting properties and excellent heat resistance, and the back surface of the electrically insulating material sheet is coated with ethylenevinyl acetate or other heat-sealable material. The thus obtained multi-layered sheet is cut into a tape form and used as an electrode tape. The thus obtained electrode tape is heat-sealed to the electrically insulating substrate (1), forming the electrode (2).

The structure wherein a two-layered substrate is used as the substrate (1) and the electrode (2) is provided on the substrate is another example of a preferable embodiment. Among the above substrate examples, a two-layered substrate obtained by laminating a polyester-based resin film and a polyimide film is preferable. This case is explained in detail below.

A PET film is one example of a polyester-based resin film and the thickness thereof is usually about 70 to 150 μm. Note that the polyester-based resin film can be used as a substrate by itself. In the present invention, an example of polyimide film which is laminated on the polyester-based resin film is a (thin) aromatic polyimide film (hereunder referred to as a PI film) having a thickness of about 20 to 50 μm.

In this method, the two electrodes are formed on the PI film in advance, and the bottom surface of the PI film and the PET film are laminated with an adhesive in between. This makes it possible to obtain the two-layered substrate and the electrodes in a single step. Thus an electrode plate having excellent heat resistance, chemical resistance, and other properties is formed.

The reason why the electrodes are formed on the PI film in advance and laminated with the PET film is as follows:

PI film is strong and has high heat resistance, and therefore it is possible to use a large quantity of very thin PI film wound on a roller, and because of its excellent adherence to the formed electrodes, the PI film is suitably used for forming the electrodes by sputtering. In other words, a long PI film can be continuously supplied from one roller to another for a long time, and therefore electrode plates with high productivity and quality can be easily obtained.

Highly pure platinum is preferably used as the good electrical conductor employed in the sputtering process. In this case, the sputtering conditions are: under argon atmosphere, degree of vacuum of about 1.3 to $1.3 \times 10^{-2}$ Pa, input power of about 0.2 to 3 kW, and sputtering rate of about 0.2 to 3.0 m/min.

The formation of electrodes by employing masking is conducted as described below. If the desired shape of the electrodes is a stripe, a mask plate having two stripe-shaped parallel holes stamped therein is used as a masking material, and this mask plate is fixed to the top of the continuously supplied PI film leaving no space between the mask plate and the PI film. Sputtering at the rate described above is started as soon as the supply of the film begins. The platinum sputtering material is delivered through the stamped stripe-shaped window, and then two continuous stripe-shaped electrodes are closely adhered onto the polyimide film. The film is supplied from one roller to another roller and taken up.

If an electrode with a certain thickness is not obtained by one sputtering cycle, sputtering may be repeated while rewinding the film.

The PI film having electrodes formed thereon is laminated onto a PET film with an adhesive lying in between. As shown in FIG. 7, a spacer sheet (5) provided with a projection (51) and an external cover sheet (6) are laminated using adhesive on the PI film in such a manner that a sample suction part (15) and a reaction part (4) are formed. After completion of the step (C2), the external cover sheet (6) covers all but the terminal provided on the other end of the biosensor.

The application liquid for forming reaction part described in the step of (B2) is then prepared. In this step, a mixed solution Ma is first prepared by adding three components, i.e., an oxidoreductase, an electron acceptor, and fine crystalline cellulose, to a good solvent within the ratios described above.

Here, the good solvent is a water-containing solvent to which the three components are dissoluble or dispersible (suspendable). An example of a good solvent is water or a mixed solution of water and a water-compatible lower monovalent aliphatic alcohol (alcohols of not more than $C_3$, etc.). Note that among the three components, the oxidoreductase and the electron acceptor are substantially dissolved into the good solvent; however, the fine crystalline cellulose may be dispersed or suspended in the good solvent.

The method for preparing the mixed solution Ma is to merely add the three components to the good solvent at the same time and stir it at an ordinary temperature. Alternatively, a sequential method as described next is also possible. First, the fine crystalline cellulose is suspended in water (distilled water) (it is preferable that suspension be conducted using a homogenizer and the concentration of the cellulose be as low as about 4 to 7 wt %), and then the other two components are added to the suspension and stirred.

A solution Pa of hydrophilic polymer is prepared in a separate step. The solvent used in the solution Pa is a solvent (good solvent) in which hydrophilic polymer can substantially be completely dissolved; however, at the same time, it is a solvent (poor solvent) in which the three components are barely soluble or substantially insoluble (hereunder sometimes referred to as a "specific solvent").

Examples of "specific solvents" are univalent aliphatic alcohols having four or more carbon atoms, bivalent or trivalent higher aliphatic polyhydric alcohols or polyhydric alcohols wherein at least one hydroxyl group of the higher aliphatic polyhydric alcohols is substituted with an alkyl group. Among these, bivalent aliphatic alcohols wherein one hydroxyl group is substituted with an alkyl group are preferable. Specifically, monomethyl or monoethyl ether of ethylene glycol is preferable. It is also possible to mix two or more of such organic solvents to control the dissolubility and dispersibility of the polymer.

The aqueous mixed solution Ma comprising the three components dissolved therein is added dropwise to the hydrophilic polymer solution Pa while stirring. It is preferable that stirring be conducted not intensely but softly and that a certain amount of the aqueous mixed solution Ma be added dropwise slowly for a given length of time. This makes it possible to produce fine crystal particles having a uniform grain diameter. Such a mixing method is particularly effective for preparing an application liquid for forming reaction part.

It is also possible to add only the "specific solvent" dropwise to an aqueous mixed solution Ma in which the three components and a hydrophilic polymer are mixed therein in advance. Alternatively, it is possible to add the hydrophilic polymer solution Pa dropwise to the aqueous solution Ma. However, a more preferable reaction part (4) can be formed by employing the steps described in Item (B2).

One of the main features of the present invention is that an application liquid for forming reaction part comprising the four components is a dispersion. Because the three components are crystalline fine powders, when a film is formed by applying the three components and drying them, these components are returned to their crystalline particle state and mixed and dispersed in the film. However, because particles with various sizes are mixed and dispersed nonuniformly, the mutual linking between the components deteriorates, adversely affecting their stability over time.

In contrast, the application liquid for forming reaction part comprising the four components is a dispersion (suspension) wherein particles are deposited in a hydrophilic polymer including an "aqueous solvent". Furthermore, the particles in a dispersion (suspension) condition have almost the same grain size and are super fine particles. When a reaction part (4) is formed by applying such an application liquid and drying it, the particles therein are kept in a dispersed condition by the hydrophilic polymer. The thus formed reaction part promptly reacts with a sample and maintains stability over a long time without being affected by the surroundings.

In the step (C2) of forming the reaction part, a predetermined amount of the application liquid for forming reaction part is applied dropwise to one end of the electrode (2) on the electrode plate obtained in the step (B2) and dried, forming a film. This film is adhered across the working electrode (21) and the counter electrode (22) and functions as the reaction part (4).

Specifically, the film is formed in the same manner as in the reaction part formation step (C1) described in item "I. Biosensor of the first invention".

A desirable biosensor is formed by following the steps of (A2) to (C2) and it is then cut into biosensor chips, completing the process.

The thus obtained biosensor of the first invention and second invention can be used for determining the quantity of a specific component in a sample solution. Specifically, the glucose component, alcohol component, lactic acid component or uric acid component in the sample solution is measured with high precision without variation. In either invention, known measurement methods for biosensors can be employed. Particularly, when the glucose component in a sample solution is measured, the method described in Example 3 is preferably employed.

III. Biosensor of the Third Invention

In the sections above, the biosensors of the first invention and second invention, which are characterized in the reaction part (4), are described in detail.

Hereinafter, the biosensor of the third invention, which is characterized in the shape of a liquid sample suction port, is described in detail with reference to FIGS. 7 to 9. The reaction part (4) of the biosensor of the third invention may comprise the same components as in the first invention or second invention.

In FIGS. 7 and 8, an electrically insulating substrate (1) of this embodiment is formed in a rectangular shape, and the tip portion is formed approximately in a semicircular shape. An electrode (2) disposed on the substrate (1) comprises a working electrode (21) and a counter electrode (22) which are arranged approximately in parallel along the longitudinal direction of the substrate (1).

In this embodiment of the invention, the electrode (2) is formed by adhering two electrode films, which is obtained by sputtering a platinum film onto a specified polyimide film, to the substrate (1) at about 0.5-mm intervals with adhesive.

An electrically insulating mask sheet (3) is laminated to the substrate (1) partially covering the electrode (2). The mask sheet (3) is provided with a substantially oval (or rectangular) reaction part cell (window) (31) at its substantially semicircular tip portion. The reaction part cell (31) exposes the tip portion of the electrode (2). The mask sheet (3) is not laminated to the rear end of the substrate (1), which exposes the rear end of the electrode (2). The exposed tip portion of the electrode (2) serves as a detection part for detecting an electrochemical change due to an enzyme reaction between the reaction part (4) and a liquid sample, which is described later. The exposed rear-end portion of the electrode (2) serves as a connection terminal to be connected to a measuring device. In this embodiment, a hot melt film, the tip portion of which is formed substantially in a semicircular shape, is used as the mask sheet (3) and is laminated to the substrate (1) by thermal pressing.

The reaction part (4) disposed on the detection part of the electrode (2) in the reaction part cell (31) of the mask sheet (3) comprises an enzyme that reacts to a specific component of the liquid sample and an electron acceptor that receives electrons that are generated during an enzyme reaction. The composition of the reaction part (4) is as described above.

At the spacer end of an electrically insulating spacer sheet (5) covering the mask sheet (3) except for the substantially semicircular tip portion of the mask sheet (3), a projection (51) extending toward the sensor tip is formed on one side in the widthwise direction of the spacer sheet. An inside corner part (52) is provided on the basal portion of the projection (51). In this embodiment, a PET-based film provided with an adhesive layer on either side is used as the spacer sheet (5) and is laminated to the mask sheet (3).

The tip portion of an electrically insulating cover sheet (6) disposed on the spacer sheet (5) is formed substantially in a semicircular shape that is slightly smaller than the tip portion of the substrate (1). At the semicircular portion of the cover sheet (6), the cover sheet (6) and the substrate (1) are disposed facing each other at a specific interval provided by the spacer sheet (5). Thus, a holding space S is formed at the sensor tip portion. The holding space S is surrounded by the upper surface of the mask sheet (3) and the reaction part (4) which are disposed on the substrate (1), the under surface of the cover sheet (6), and the spacer end of the spacer sheet (5). In this embodiment, a transparent PET-based film is laminated to the upper surface of the spacer sheet (5) for use as the cover sheet (6).

A liquid sample is measured using the biosensor (10) thus configured as follows. First, a measuring device is attached to the rear end of the biosensor (10). The liquid sample to be measured is then brought into contact with a sample suction port (15) formed at the tip of the biosensor (10). The liquid sample is then introduced into the holding space S by capillary action. Subsequently, in the holding space S, a specific component of the liquid sample and the reaction part (4) are subjected to an enzyme reaction. The electrochemical change caused by the reaction is detected by the electrode (2), and the specific component of the liquid sample is measured by the measurement device.

Since the biosensor (10) is provided with a projection (51) at one side of the end of the spacer sheet (5), the liquid sample that flows from the sample suction port (15) at the sensor tip by capillary action can be initially made to contact the projection (51). The wettability of the projection (51) can facilitate the introduction of the liquid sample by its capillary action. Accordingly, as shown in FIG. 9, after the front edge F of the liquid sample flowing from the side of the sample suction port (15) at the sensor tip contacts the projection (51), the liquid sample can be flowed preferentially from one side along the side surface of the projection (51). Thus, the liquid sample can be smoothly introduced throughout the holding space S while discharging gas in the holding space S to the side opposite the projection (51) (see the arrow C in FIG. 3).

When gas is discharged to the side opposite the projection (51), the discharged air current C can avoid the generation of bubbles resulting from the contact of the liquid sample with the spacer sheet (5) at any portion besides the projection (51). Thus, the liquid sample can be introduced to the holding space S without leaving bubbles therein.

According to the biosensor (10), the liquid sample can be introduced from one side along the projection (51) because the projection (51) can facilitate the introduction. Thus, even if an inside corner part (52) is formed at the spacer sheet (5) at the innermost part of the holding space S, no bubbles are left in the inside corner part (52). This makes it possible to form the inside corner part with an adequate area in the biosensor (10), however the area of the inside corner part is limited in the prior-art biosensor due to the problem of remaining bubbles. The formation of the inside corner part can easily enlarge the capacity of the holding space S.

In the biosensor (10), the cover sheet (6) can be supported by the projection (51) extending toward the sample suction port (15) at the sensor tip, thereby stably maintaining a set interval between the substrate (1) and the cover sheet (6). Thus, deformation of the cover sheet (6) due to, for example, temperature changes or external forces can be prevented, and further a specified amount of the liquid sample can be introduced into the holding space S. Therefore, accurate measurement can be made with reduced measurement error.

BRIEF DESCRIPTION OF THE DRAWINGS

FIG. 7 (a) is a plane view and FIG. 7 (b) is a cross-sectional view of FIG. 7 (a) taken along the line A-A.

BEST MODE FOR CARRYING OUT THE INVENTION

Figure 1:
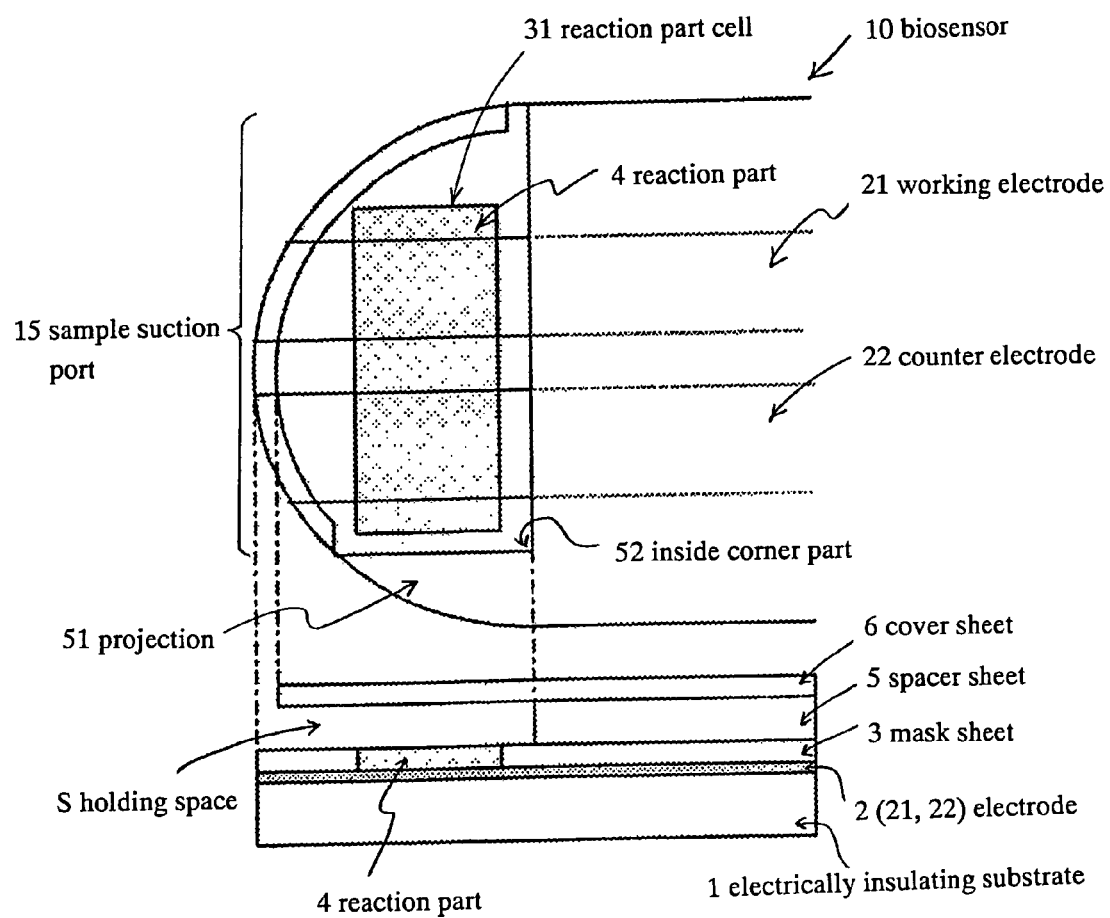
FIG. 1 illustrates an example of the configuration of the sensor tip.

The invention is described in detail with reference to Examples and Comparative Examples. However, the invention is not limited to these examples.

I. Biosensor of the First Invention

First, the measurement principle used in the Examples is explained.

The measurement system in the Examples comprises a disposable sensor tip and a measurement body, and employs the enzyme electrode method.

The reaction of the measurement is represented by the following formula.

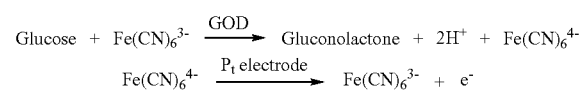

Glucose in blood is oxidized with a glucose oxidizing enzyme (GOD), producing gluconolactone. During this process, a potassium hexacyano iron (III) (potassium ferricyanide) acceptor is reduced, producing hexacyano iron (II) (ferrocyanide) ions. The generated ferrocyanide ions are oxidized to ferricyanide ions in the vicinity of an energized platinum electrode, thereby generating electrons. The current value of the generated electrons is used to calculate the glucose concentration.

Example 1

(a) Preparation of Sensor Structural Elements

Platinum was sputtered onto a polyimide sheet. The back of this polyimide sheet was coated with ethylene vinyl acetate (EVA) as a heat sealable material. The obtained multilayer sheet was cut into tape-like sheets. Each of the obtained sheets was used as a platinum electrode tape. A hole (a reaction part cell) was provided in a polyester-based hot-melt-adhesive sheet in such a manner to determine the electrode surface area of sensor tip reaction parts, forming a mask sheet. The platinum electrode tape and the mask sheet were then thermally adhered to a white PET sheet as an insulating material. A space was formed in a double-sided adhesive sheet having an acryl-based adhesive layer (25 μm in thickness) on either side of a PET layer (100 μm in thickness) in such a manner to form a sample suction space, providing a spacer sheet.

(b) Preparation of an Application Liquid for Forming Reaction Part 100 g of a ceolus cream (ceolus cream FP-03, manufactured by Asahi Kasei Corporation, 10% by weight of crystalline cellulose) was added to 150 g of distilled water, and the mixture was stirred at 10000 rpm for 15 minutes by a homogenizer, producing a ceolus cream diluent.

To the thus obtained ceolus cream diluent was added 2.44 g of glucose oxidase (manufactured by Toyobo Co., Ltd., activity: 165 unit (u)/mg) and 40 g of potassium ferricyanide (manufactured by Nacalai Tesque, special grade), and the mixture was stirred by a magnetic stirrer at 500 rpm for 15 minutes, producing mixed solution A.

100 mL of the thus obtained solution A was gently added dropwise to 100 mL of ethylene glycol monoethylether (manufactured by Nacalai Tesque, special grade) while stirring at 500 rpm by a magnetic stirrer. After the addition of the solution A was complete, the mixture was stirred for 5 minutes, producing dispersion B. The dispersion B thus obtained was used as a reaction part-forming application liquid.

(c) Application and Drying of the Application Liquid for Forming Reaction Part A base sheet was obtained by laminating the electrode tape (a) to the mask sheet. One μL of the application liquid for forming reaction part obtained in the above (b) was applied, using a pipette, to the mask sheet reaction part cell disposed on the base sheet.

The above-described base sheet was then put into an oven and dried for 10 minutes. After drying, a reaction part was formed.

(d) Sensor Tip Formation

Figure 2:
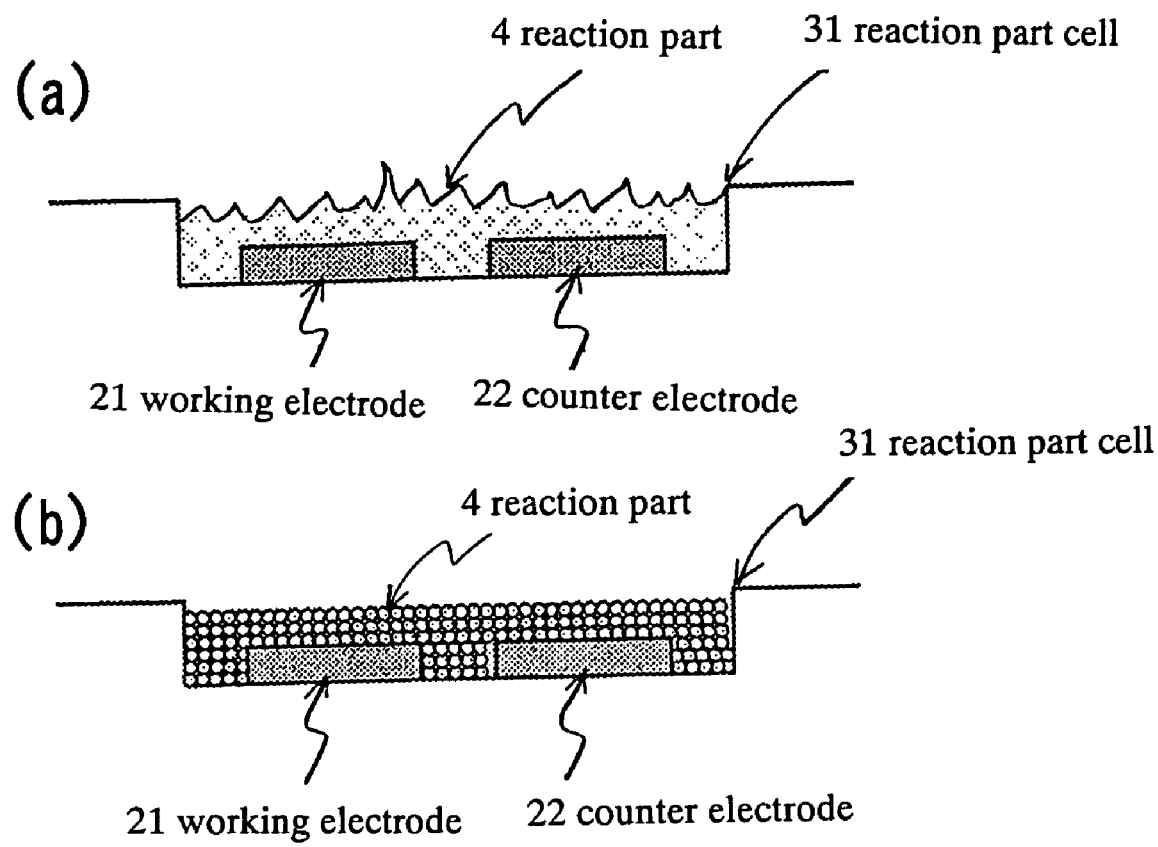
FIG. 2 is a schematic cross-sectional view illustrating the reaction part of Example 1 and Comparative Example 1.
Figure 4:
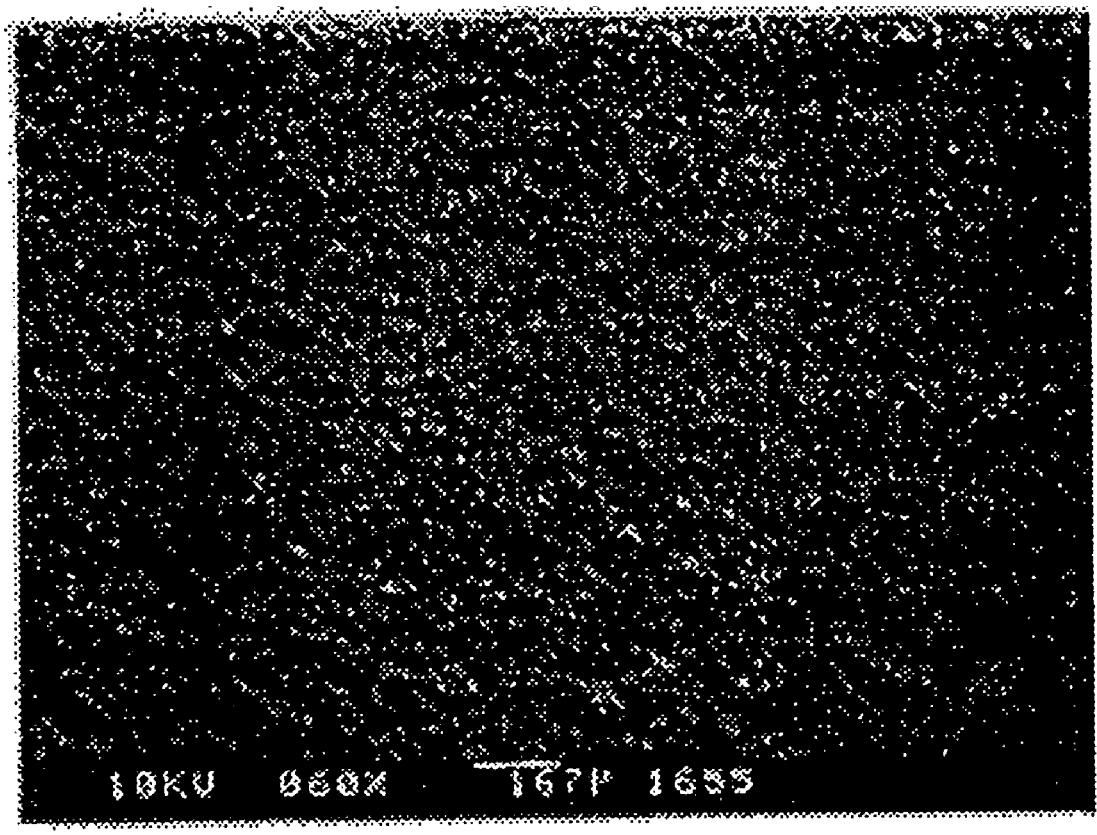
FIG. 4 is a copy of an electron microscope photograph showing the surface condition of the reaction part of Example 1.

The spacer sheet obtained in (a) above and a cover sheet were laminated in this order onto the base sheet obtained in (c) above. The laminate was punched into ten sensor chips. FIG. 4 is an electron microscope photograph showing the surface condition of the reaction part. FIG. 2 (b) schematically illustrates the cross section of the reaction part of FIG. 4.

(e) Measurement

The following measurement was performed using the sensor chip obtained in (d) above.

The induced current which flows when the reaction part of the sensor chip dissolves in a sample solution was measured to evaluate the solubility of the sensor chip. More specifically, the Faraday current was measured for the ten sensor chips to evaluate their solubility, and it was found that the average value was 160.1 (Table 1 and FIG. 5).

Figure 6:
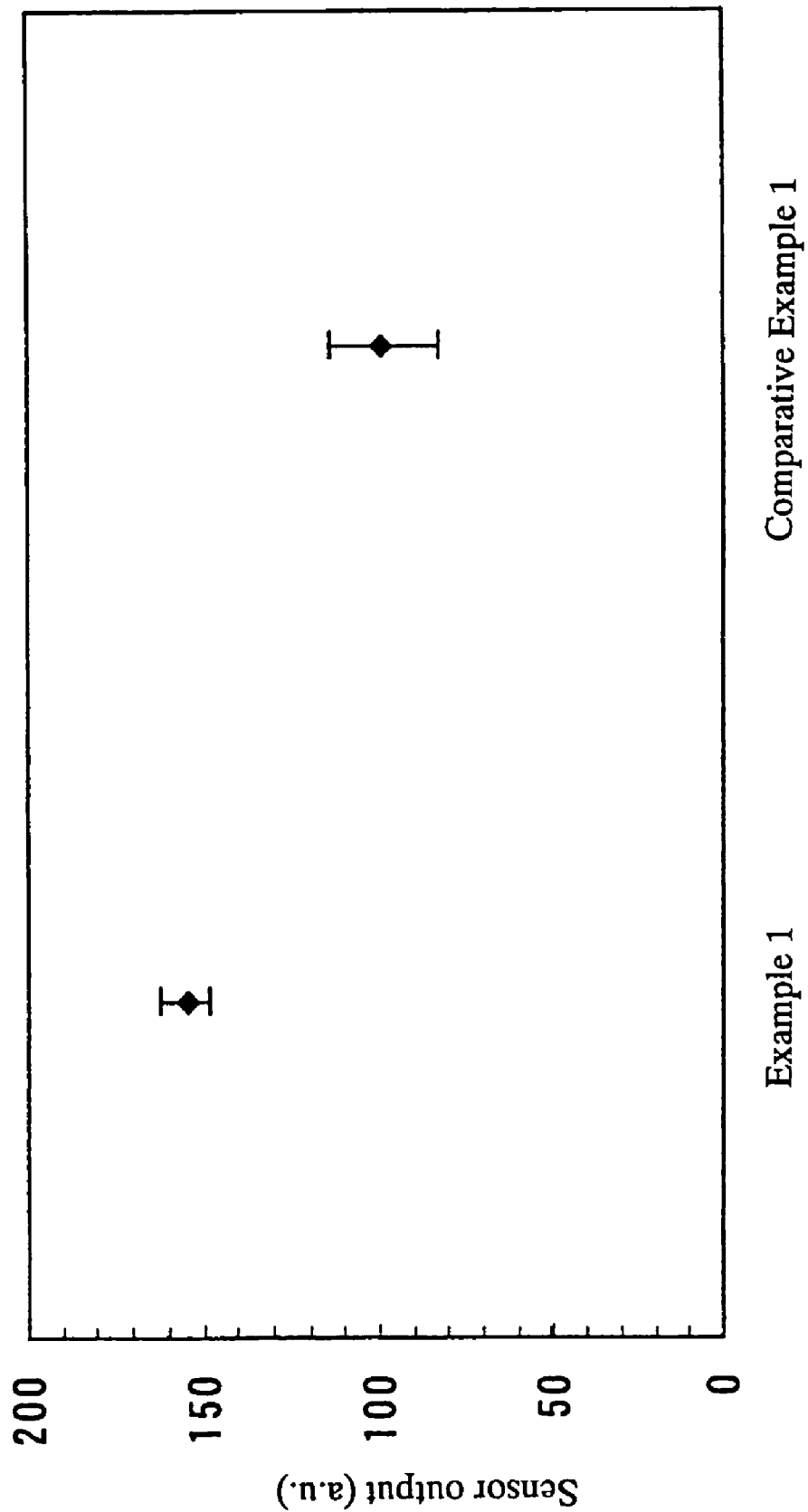
FIG. 6 is a diagram showing a comparison of sensor output between Example 1 and Comparative Example 1.

The sensor output was measured, and it was found that the output sensitivity at a glucose concentration of 100 mg/dL and measuring time of 20 seconds was 154.7 (Table 2 and FIG. 6).

The output variation was measured among the individual sensor chips and it was found that the CV value was 3% (Table 2 and FIG. 6). The CV value in this specification denotes a value obtained by the formula: (Standard deviation of sensor outputs/Average value of sensor outputs)×100.

Comparative Example 1

Figure 3:
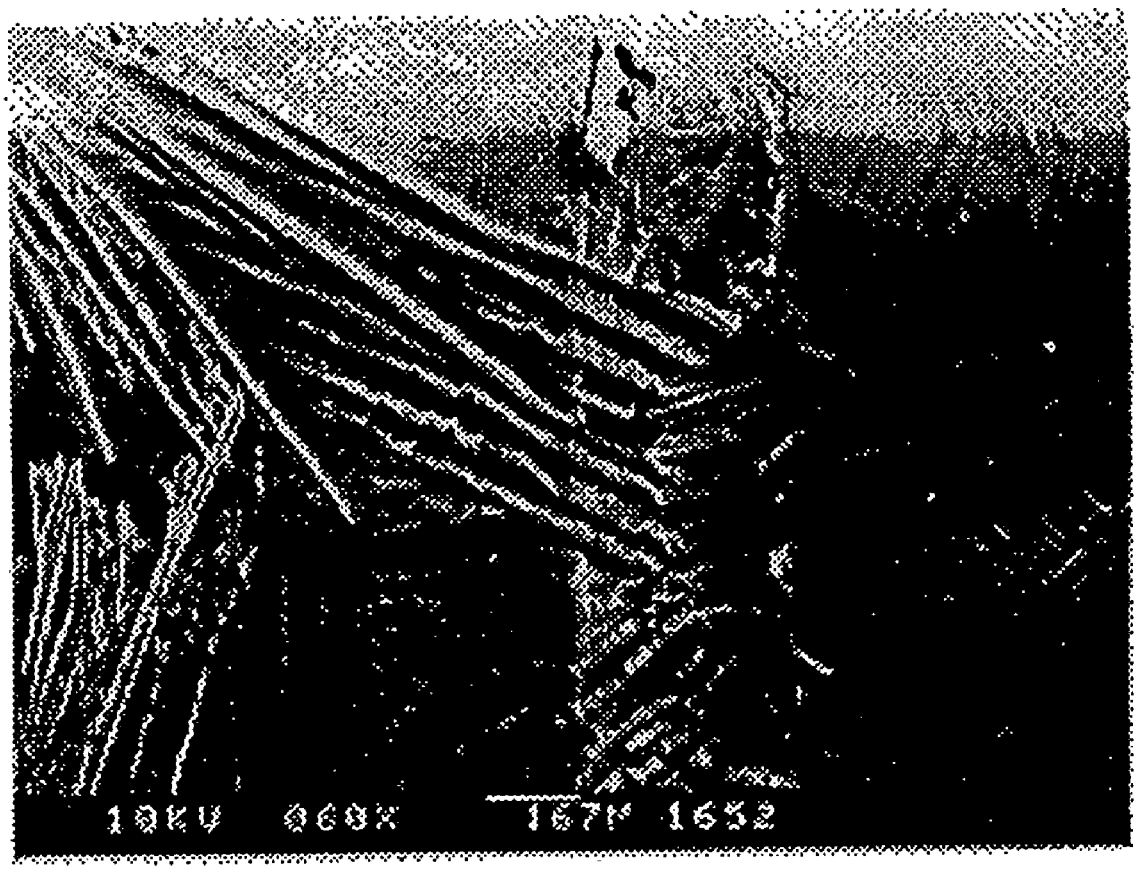
FIG. 3 is a copy of an electron microscope photograph showing the surface condition of the reaction part of Comparative Example 1.

Solution A was obtained in the same manner as in Example 1. Ten sensor chips were produced in the same manner as in Example 1 except that the solution A was used as the reaction part-forming application liquid. FIG. 3 is an electron microscope photograph showing the surface condition of the reaction part. FIG. 2(a) schematically illustrates the cross section of the reaction part shown in FIG. 3.

Figure 5:
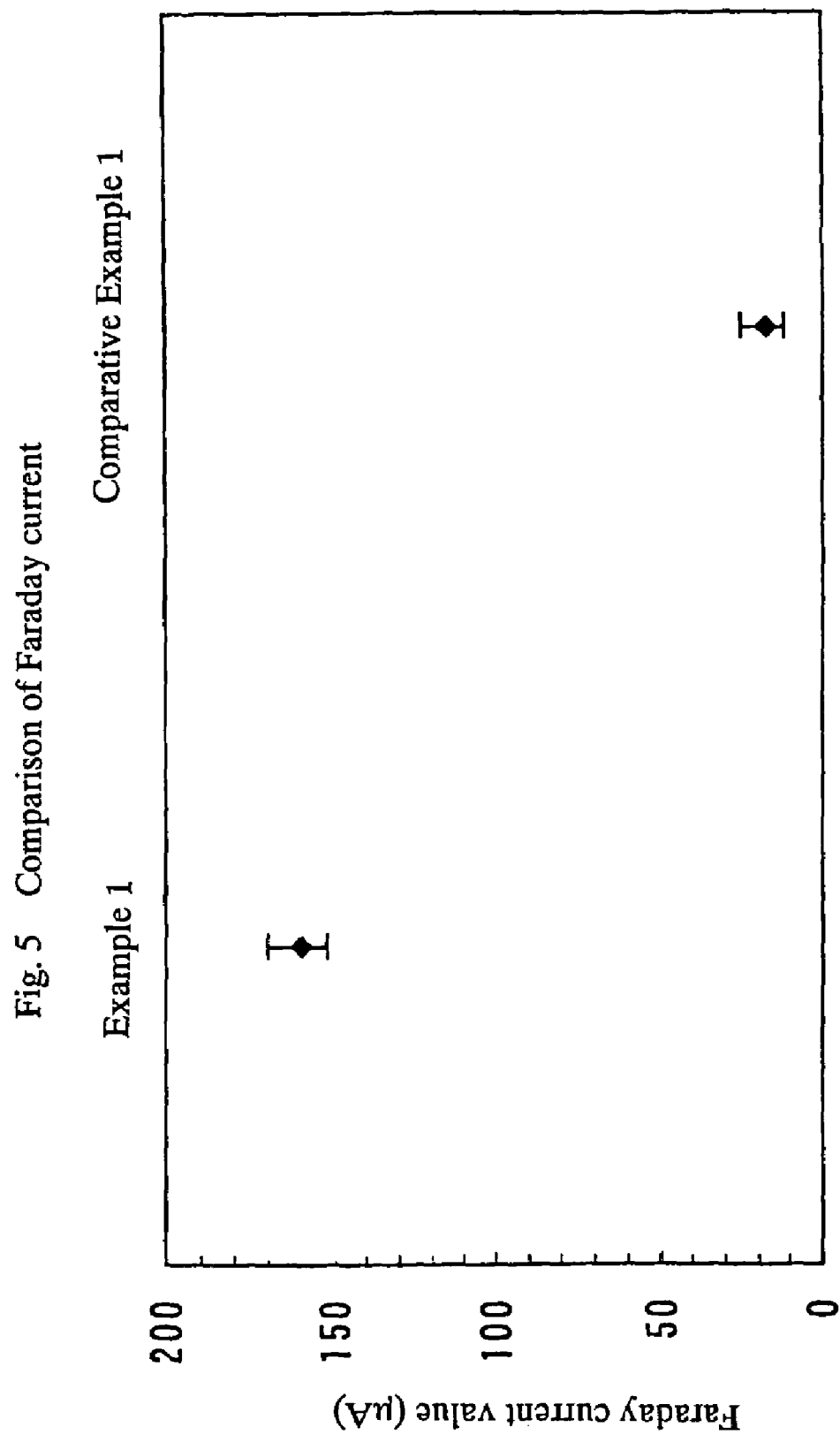
FIG. 5 is a diagram showing a comparison of Faraday current between Example 1 and Comparative Example 1.

The solubility of the ten sensor chips was evaluated by measuring the Faraday current in the same manner as in Example 1, and it was found that the average value was 17.6 (Table 1 and FIG. 5).

The sensor output sensitivity at a glucose concentration of 100 mg/dL and measuring time of 30 seconds was 99.2 (Table 2 and FIG. 6).

The output variation was measured among the individual sensor chips and it was found that the CV value was 10% (Table 2 and FIG. 6).

As can be seen from FIG. 5, the solubility of the reaction part of the sensor chip of Example 1 is much larger than that of the sensor chip of Comparative Example 1.

FIG. 6 shows that the sensor output of the sensor chip of Example 1 is larger than that of Comparative Example 1, which shows that the sensor chip of Example 1 has a higher level of reliability than that of Comparative Example 1. The output variation of the sensor chips of Example 1 was also less than that of the sensor chips of Comparative Example 1.

TABLE 1

Faraday current comparison

|  | Example 1 | Comp. Example 1 |
|---|---|---|
| 1 | 156 | 12 |
| 2 | 155 | 19 |
| 3 | 159 | 25 |
| 4 | 168 | 18 |
| 5 | 152 | 15 |
| 6 | 155 | 20 |
| 7 | 166 | 16 |
| 8 | 170 | 18 |
| 9 | 162 | 17 |
| 10 | 158 | 16 |
| Average value | 160.10 | 17.60 |
| CV value (%) | 3.83 | 19.72 |
| Standard deviation | 6.14 | 3.47 |
| MAX | 170 | 25 |
| MIN | 152 | 12 |
| MAX-MIN | 9.90 | 7.40 |
| Average-MIN | 8.10 | 5.60 |

TABLE 2

Sensor output comparison

|  | Example 1 | Comp. Example 1 |
|---|---|---|
| 1 | 156 | 94 |
| 2 | 149 | 114 |
| 3 | 159 | 100 |
| 4 | 151 | 89 |
| 5 | 152 | 104 |
| 6 | 155 | 101 |
| 7 | 148 | 105 |
| 8 | 160 | 92 |
| 9 | 162 | 83 |
| 10 | 155 | 110 |
| Average value | 154.70 | 99.20 |
| CV value (%) | 3.05 | 9.75 |
| Standard deviation | 4.72 | 9.67 |
| MAX | 162 | 114 |
| MIN | 148 | 83 |
| MAX-MIN | 7.30 | 14.80 |
| Average-MIN | 6.70 | 16.20 |

II. Biosensor of the Second Invention

The following examples are described in accordance with Item 9, which presents a favorable mode of embodiment for producing the biosensor of the invention.

Example 2

The electrode formation process (A2) was carried out as described below.

Figure 7:
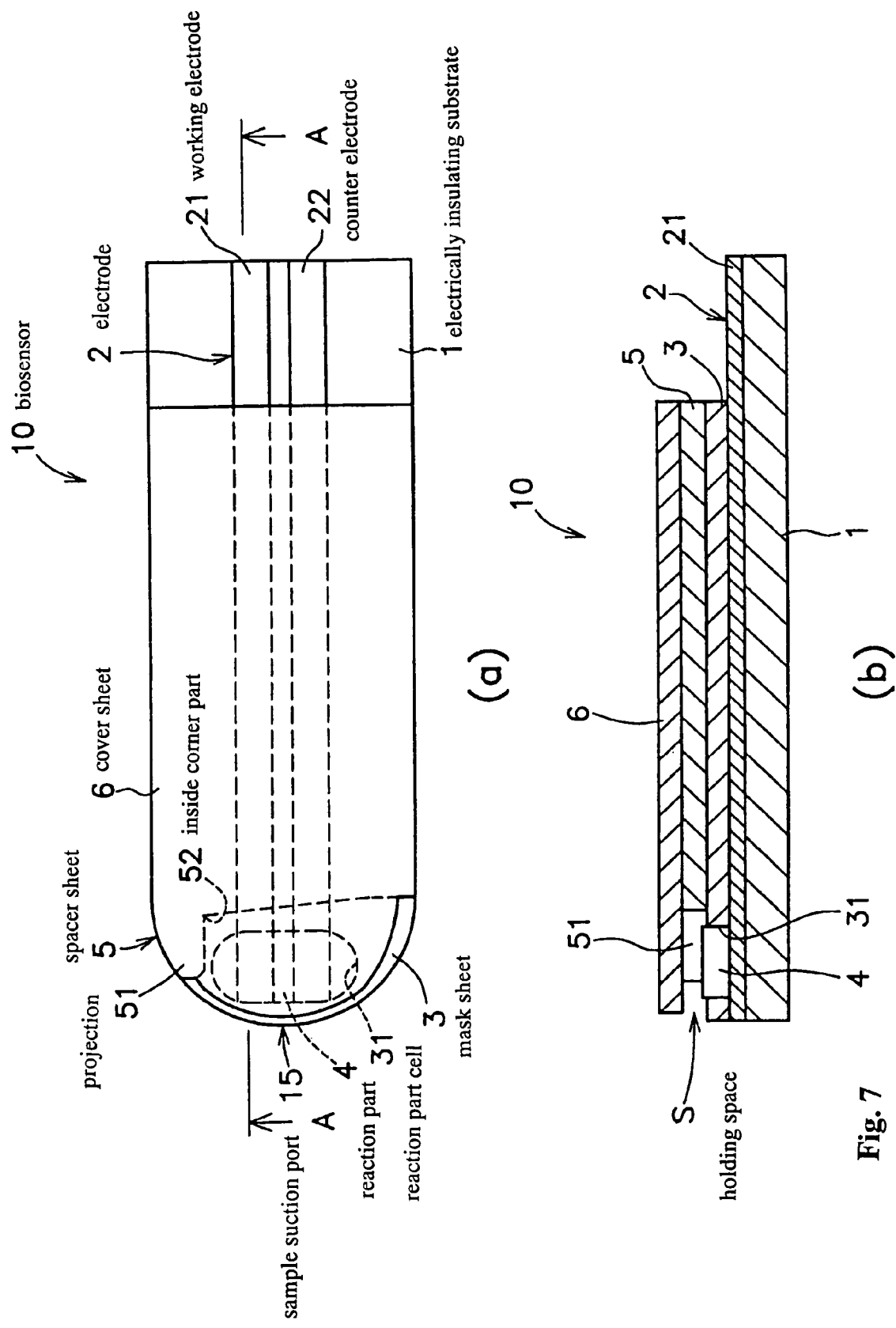
FIGS. 7 (a) and (b) show examples of the biosensor of the invention.

One hundred enzyme sensors with the configuration shown in FIG. 7 were produced with the following kind of method.

A working electrode (21) and a counter electrode (22) which have a thickness of 0.06 µm and a size of 1×35 mm were formed by sputtering platinum at intervals of 1 mm on a polyimide film of 25 µm in thickness, and this was laminated with a white PET film (1) of 250 µm in thickness using adhesive. At one end of the side on which both of these electrodes were formed, the electrodes were left uncovered to serve as a terminal (21a and 22a), and to the remaining portion thereof, a 100 µm-thick PET film (electrically insulating spacer sheet (5)) was laminated using adhesive, the PET film being provided with a rectangular window (reaction part cell (31)) large enough to extend over the two electrodes (1.5×5 mm) (compartment to be used as a reaction part (4)) and a sample suction port (15) to serve as a suction path for leading a test sample to the rectangular window.

The preparation process for the application liquid for forming reaction part (B2) was carried out as described below.

The following four substances were used as essential ingredients:

Oxidoreductase: 2.44 g of glucose oxidase (manufactured by Toyobo Co., Ltd., activity: 165 unit (u)/mg (hereinafter referred to as an experimental enzyme);

Electron acceptor: 40 g of purified potassium ferricyanide (manufactured by Nacalai Tesque (hereinafter referred to as an experimental electron acceptor);

Fine crystalline cellulose suspension: suspension of 100 g of ceolus cream ("FP-03", manufactured by Asahi Kasei Corporation, 10% by weight of crystalline cellulose) and 150 ml of distilled water (hereinafter referred to as an experimental cellulose suspension); and Hydrophilic polymer solution: Block polymer comprised of ethylene oxide and propylene oxide, in which the average molecular weight of an oxypropylene glycol unit is about 2050, the ethylene oxide content of all molecules is about 50% by weight, and the appearance is paste-like (20° C.). 7.5 g of such polymer was uniformly dissolved into 100 ml of ethylene glycol monoethyl ether (hereinafter referred to as an experimental hydrophilic polymer solution Pa).

The above experimental enzyme and experimental electron acceptor were added to the experimental cellulose suspension, thereby obtaining a mixed solution of three components. The obtained mixture is referred to as a mixed solution Ma.

The mixed solution Ma was gently added dropwise to the experimental hydrophilic polymer solution Pa while stirring. After the dropwise addition was complete, stirring was continued for 5 minutes and then stopped. The condition of the mixture thoroughly changed to an aqueous suspension due to the precipitation of particulates. The aqueous suspension was used as an application liquid for forming a reaction part.

Finally, in the process for forming a reaction part (C2), a reaction part (4) was formed to obtain 100 pieces of desired biosensors.

More specifically, 1 μL of the above application liquid for forming a reaction part was gently added dropwise using a pipette to the rectangular reaction part cell (31) formed on a plate with platinum electrodes obtained in the above-described process (A2) and was dried, thereby adhering a reaction part membrane (in which the membrane surface has no tackiness) to the cell. Finally, an outside cover sheet (6) made of a PET film was adhered and laminated thereto with adhesive (except the parts corresponding to the reaction part and sample suction port) while leaving the terminals (21*a* and 22*a*) uncovered. The resulting laminate was cut into chips, thereby producing the desired 100 enzyme sensor chips.

Comparative Example 2

The same procedure was conducted as in Example 2 except that a hydrophilic polymer was not used. More specifically, a reaction part-forming application liquid for comparison was prepared (an aqueous liquid with the same appearance as in Example 2). The prepared liquid was applied to a reaction part cell (31) on a plate with platinum electrodes to obtain a reaction part membrane, thereby producing 100 enzyme sensor chips for comparison.

Example 3

Using 20 of the enzyme sensor chips (randomly selected) obtained in Example 2 and Comparative Example 2, the terminals (21*a* and 22*a*) thereof were connected to an enzyme sensor measurement device, and the current corresponding to the scanning potential was measured under the following conditions.

A glucose solution with a concentration of 100 mg/dL was used as a sample. Ten enzyme sensor chips were preserved for days and other ten chips were preserved for 40 days. Five μL of the test sample was injected into the suction port of each of the ten chips. After 8 seconds had passed, an electric potential was applied with continuous variation in the manner of 0V→-0.2V→+0.2V at a scanning rate of 50 mv/s. The current was measured during this application of electric potential. The output sensitivity based on the current corresponding to each of the different potential values applied was measured. FIG. 3 shows the average value of the output sensitivity of each of the ten chips.

Output sensitivity is an integral value of the current value (integrated current value) between the applied electric potential of −0.2V→+0.2V. This value serves as an index to show the efficiency with which the reaction deviation of a test sample at the reaction part is promptly and surely input to an electrode. Accordingly, the larger the value is, the more the reaction deviation is input. In general, it is needless to say that the reactivity between the test sample component and the reaction part is important. It is extremely important from the viewpoint of measurement accuracy that all of the reaction deviation be input to the electrode if possible.

TABLE 3

|  | 5 days | 40 days |
| --- | --- | --- |
| Example 2 | 128 | 127 |
| Comp. Example 2 | 92 | 81 |

Subsequently, 35 chips were sampled from the remaining enzyme sensor chips (randomly selected). The same test sample as above was used, and the measurement was carried out under the following conditions. The generated output was measured at each measurement day to obtain the output variation, which is shown in the graph of FIG. 10.

Initially, 35 sensor chips were left standing in a storage container with a desiccating agent at room temperature for a single day to 60 days. Five chips were taken out of the container at each measurement day, and 5 μL of the test sample was injected into each of the 5 chips. The generated output was then measured under the same measurement conditions as in Example 1. The generated output of each of the sensor chips measured at each measurement day (the average value of the five generated output values) was divided by the generated output (the average value of the five outputs) of the sensor chip after one day had passed, to obtain the output variation.

Figure 10:
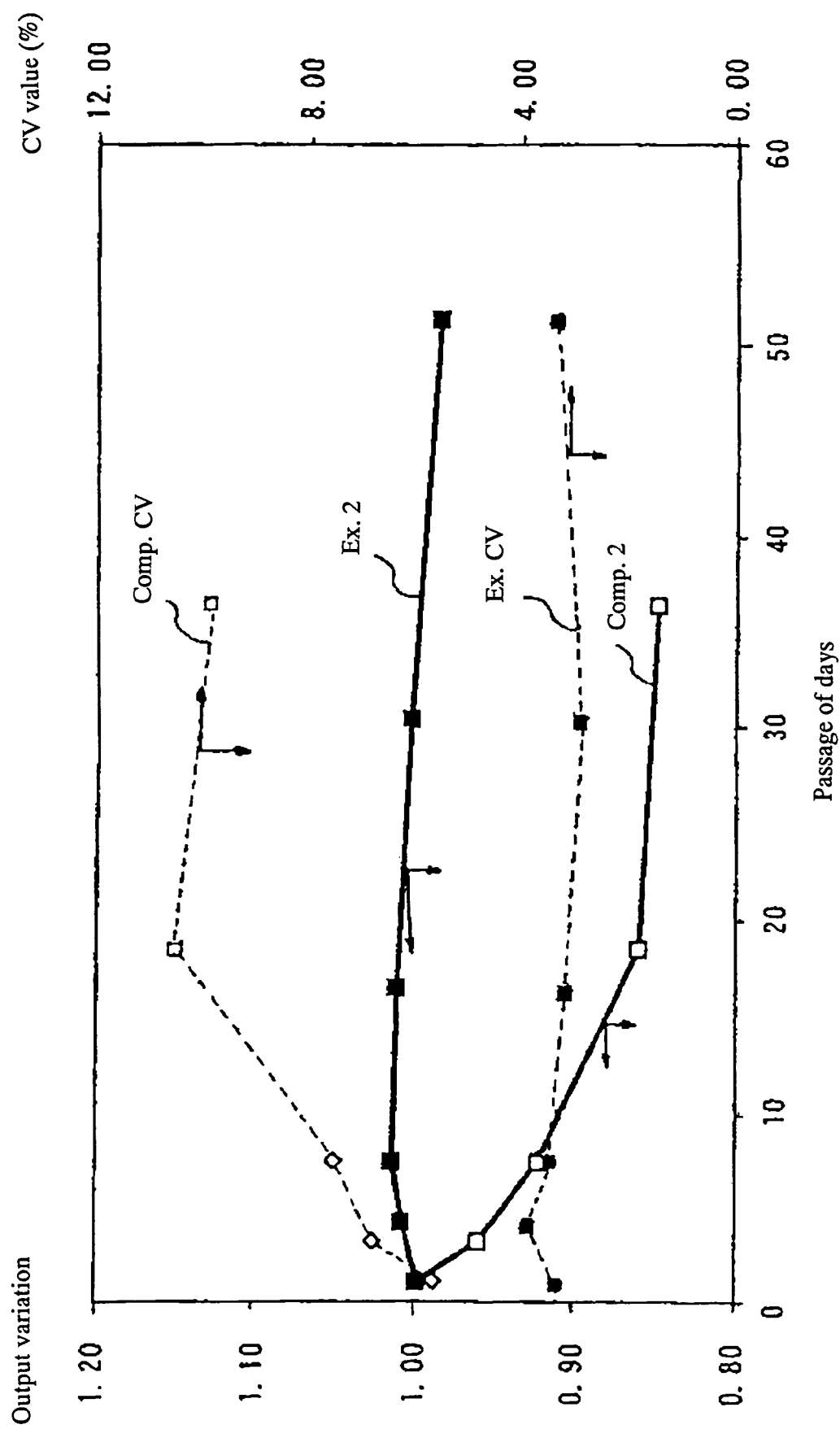
FIG. 10 is a graph illustrating variations in the output and CV values of an enzyme sensor with the passage of days.

In FIG. 10, Ex. 2 denotes Example 2, and Comp. Ex. 2 denotes Comparative Example 2. FIG. 10 shows that the output variation of the sensor chips of Example 2 is negligible as compared to that of Comparative Example 2. With respect to the sensor chips of Comparative Example 2, the measurement stopped at the 36$^{th}$ day because the difference between Example 2 and Comparative Example 2 was remarkable.

Figure 8:
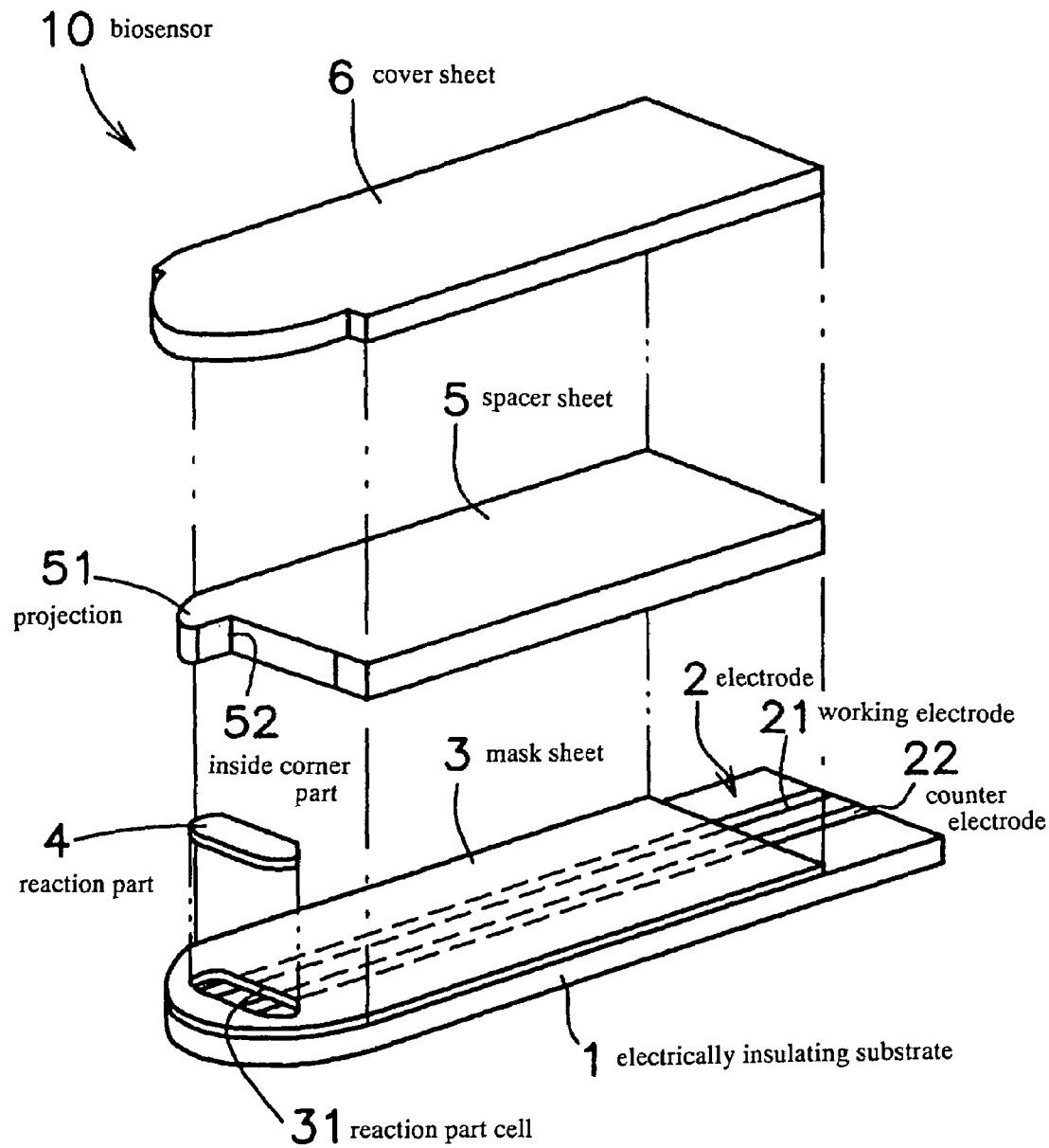
FIG. 8 is an exploded perspective view illustrating the biosensor of the invention.
Figure 9:
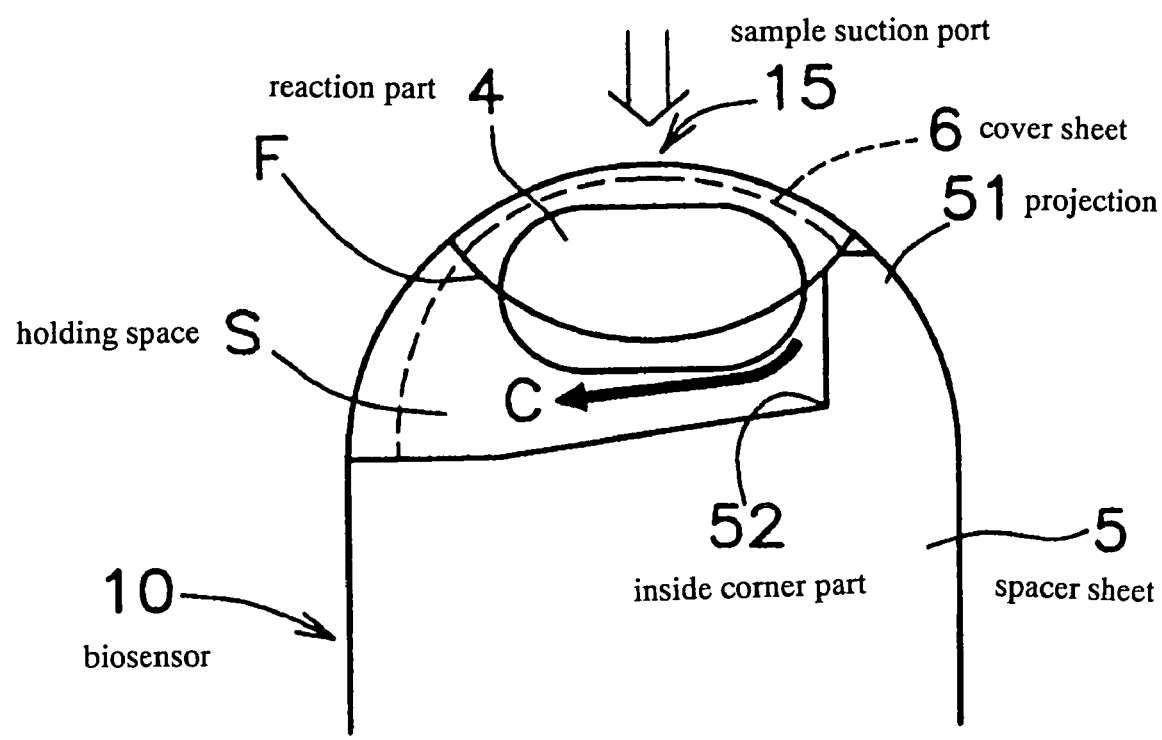
FIG. 9 is a plane view partially illustrating the introduction process when a liquid sample is introduced into the holding space of the biosensor of the invention.

The CV value (%) was measured from the output variation of the outputs of the five sensor chips measured at each measurement day. The CV values are shown in the graph of FIG. 8. In FIG. 8, Ex. CV denotes the CV value of Example 2 and Comp. CV denotes that of Comparative Example 2.

The CV value was obtained by calculating the standard deviation from variations in outputs of the five sensor chips measured at each measurement day, dividing this by the average current value, and multiplying the result by 100.

As is demonstrated by the above experiment results, the variation in the sensor chips of Example 2 is negligible and the long-term storage stability thereof is excellent as compared to those of Comparative Example 2.

INDUSTRIAL APPLICABILITY

According to the biosensor of the first invention, the solubility of the sensor chip reaction part with a sample is highly increased because the reaction part is formed using a suspension-like reaction part-forming application liquid produced by precipitation. As compared to prior-art biosensors produced by a method other than precipitation, there are no variations between biosensors and measurement accuracy is greatly increased. The increased solubility with a sample can shorten the measuring time.

According to the biosensor of the second invention, even if the biosensor is stored for a long period, the reactivity with the sample component is scarcely changed, thereby achieving measurement with high precision. This simplifies the production control, inventory control, and handling of such biosensors by users. Further, reaction results with a sample can be more accurately and efficiently measured, thereby providing a biosensor with improved precision.

The biosensor of the invention is characterized in the configuration of the sample suction port. More specifically, a projection formed at one side of an inner part of a holding space facilitates introduction of a liquid sample by its capillary action at one side of the holding space. This eliminates the need to form an outlet for discharging gas at the inner part of the holding space, which is required in prior-art biosensors. Thus, by this extremely simplified configuration, a liquid sample can be smoothly introduced into the holding space without leaving bubbles therein.

The invention claimed is:

1. A biosensor comprising:

in its tip portion, an electrically insulating substrate and a cover sheet facing each other with a space in between and a spacer sheet somewhere therebetween; and a reaction part having an oxidoreductase in a holding space formed by the substrate, the cover sheet and a spacer sheet end;

the liquid sample being delivered from the tip of the sensor into the holding space by capillary action, and an electrochemical change caused by an enzyme reaction between the liquid sample and the reaction part being detected using an electrode set having a working electrode and a counter electrode;

the biosensor being provided with a projection at only one side in the widthwise direction of the spacer sheet end in the holding space with the projection extending toward the tip portion of the biosensor;

the biosensor lacking an outlet for discharging gas in the holding space;

the spacer sheet consisting of one sheet; and the electrode being disposed on the substrate.

2. A biosensor according to claim 1, wherein an inside corner part is formed on the spacer sheet end and is provided on the basal portion of the projection so as to enlarge the capacity of the holding space.

3. A method for measuring the glucose component, alcohol component, lactic acid component or uric acid component in a sample solution comprising:

exposing the sample solution to the biosensor of claim 1, and measuring the quantity of glucose component, alcohol component, lactic acid component or uric acid component in said sample solution.

4. A biosensor according to claim 1, wherein the working electrode and the counter electrode are arranged approximately in parallel along the longitudinal direction of the substrate.

5. A biosensor according to claim 1, wherein the tip portion of the sensor is formed approximately in a semicircular shape.

* * * * *